(12) United States Patent
Leopold et al.

(10) Patent No.: US 6,716,223 B2
(45) Date of Patent: Apr. 6, 2004

(54) RELOADABLE SHEATH FOR CATHETER SYSTEM FOR DEPLOYING VASOOCCLUSIVE DEVICES

(75) Inventors: Eric Leopold, Redwood City, CA (US); Bruce McEvers, San Jose, CA (US)

(73) Assignee: Micrus Corporation, Mountain View, CA (US)

( * ) Notice: Subject to any disclaimer, the term of this patent is extended or adjusted under 35 U.S.C. 154(b) by 0 days.

(21) Appl. No.: 09/990,759

(22) Filed: Nov. 9, 2001

(65) Prior Publication Data

US 2003/0093085 A1 May 15, 2003

(51) Int. Cl.⁷ .................. A61M 29/00; A61F 2/06
(52) U.S. Cl. .................. 606/144; 606/192; 623/1.11
(58) Field of Search .................. 606/108, 192, 606/194, 198, 191, 195; 623/1.11, 1.23; 132/251, 252

(56) References Cited

U.S. PATENT DOCUMENTS

| | | |
|---|---|---|
| 1,621,159 A | 3/1927 | Evans |
| 4,306,562 A | 12/1981 | Osborne |
| 4,430,081 A | 2/1984 | Timmermans |
| 4,748,982 A | 6/1988 | Horzewski et al. |
| 4,775,371 A | 10/1988 | Mueller, Jr. |
| 5,026,377 A | 6/1991 | Burton et al. |
| 5,035,706 A | 7/1991 | Giantureo et al. |
| 5,040,548 A | 8/1991 | Yock |
| 5,061,273 A | 10/1991 | Yock |
| 5,071,407 A | 12/1991 | Termin et al. |
| 5,135,535 A | 8/1992 | Kramer |
| 5,154,725 A | 10/1992 | Leopold |
| 5,184,627 A | 2/1993 | de Toledo |
| 5,217,482 A | 6/1993 | Keith |
| 5,222,970 A | 6/1993 | Reeves |
| 5,230,348 A | 7/1993 | Ishibe et al. |
| 5,242,396 A | 9/1993 | Evard |
| 5,275,173 A | 1/1994 | Samson et al. |
| 5,279,562 A | 1/1994 | Sirhan et al. |
| 5,293,713 A | * 3/1994 | Ahmed .................. 47/55 |
| 5,299,367 A | * 4/1994 | Johnson et al. .................. 34/95 |
| 5,300,085 A | 4/1994 | Yock |
| 5,324,304 A | 6/1994 | Rasmussen |
| 5,346,505 A | 9/1994 | Leopold |
| 5,350,395 A | 9/1994 | Yock |
| 5,372,138 A | 12/1994 | Crowley et al. |
| 5,373,856 A | 12/1994 | Grenouillet |
| 5,380,304 A | 1/1995 | Parker |

(List continued on next page.)

FOREIGN PATENT DOCUMENTS

FR 2 631 835 A1 12/1989

*Primary Examiner*—Pedro Philogene
*Assistant Examiner*—D. Austin Bonderer
(74) *Attorney, Agent, or Firm*—Fulwider Patton Lee & Utecht, LLP

(57) ABSTRACT

The introducer sheath can be loaded onto a vasoocclusive device after removal of the vasoocclusive device from a microcatheter, to permit the vasoocclusive embolic coil assembly to be used again during a clinical procedure. The sheath includes a hollow, elongated tubular member with a longitudinal slot formed in the upper wall of the elongated tubular member and extending along the length of elongated tubular member. The upper wall of the elongated tubular member adjacent to the slot has an angled configuration to accept the vasoocclusive device. The sheath may include wing members extending outwardly from the angled configuration on the outside surface of the hollow, elongated tubular member to facilitate insertion of the vasoocclusive device into the sheath. The elongated tubular member may also consist of a segment with no slot attached to a flexible pusher member to facilitate initiation of loading of the vasoocclusive device into the sheath.

7 Claims, 2 Drawing Sheets

U.S. PATENT DOCUMENTS

| | | |
|---|---|---|
| 5,387,193 A | 2/1995 | Miraki |
| 5,389,087 A | 2/1995 | Miraki |
| 5,391,172 A | 2/1995 | Williams et al. |
| 5,400,785 A | 3/1995 | Crowley |
| 5,415,178 A | 5/1995 | Hsi et al. |
| 5,415,664 A | 5/1995 | Pinchuk |
| 5,421,338 A | 6/1995 | Crowley et al. |
| 5,451,233 A | 9/1995 | Yock |
| 5,456,680 A | 10/1995 | Taylor et al. |
| 5,458,613 A | 10/1995 | Gharibadeh et al. |
| 5,480,423 A | 1/1996 | Ravenscroft et al. |
| 5,489,271 A | 2/1996 | Andersen |
| 5,496,346 A | 3/1996 | Horzewski et al. |
| 5,501,227 A | 3/1996 | Yock |
| 5,507,769 A | 4/1996 | Marin et al. |
| 5,516,336 A | 5/1996 | McInnes et al. |
| 5,527,336 A | 6/1996 | Rosenbluth et al. |
| 5,531,690 A | 7/1996 | Solar |
| 5,533,968 A | 7/1996 | Muni et al. |
| 5,549,109 A | 8/1996 | Samson et al. |
| 5,549,556 A | 8/1996 | Ndondo-lay et al. |
| 5,567,203 A | 10/1996 | Euteneuer et al. |
| 5,571,094 A | 11/1996 | Sirhan |
| 5,578,009 A | 11/1996 | Kraus et al. |
| 5,603,694 A | 2/1997 | Brown et al. |
| 5,626,600 A | 5/1997 | Horzewski et al. |
| 5,662,712 A | 9/1997 | Pathak et al. |
| 5,700,253 A | 12/1997 | Parker |
| 5,735,816 A | 4/1998 | Lieber et al. |
| 5,749,921 A | 5/1998 | Lenker et al. |
| 5,759,173 A | 6/1998 | Preissman et al. |
| 5,807,398 A | 9/1998 | Shaknovich |
| 5,868,706 A | 2/1999 | Cox |
| 5,967,194 A * | 10/1999 | Martin ............... 138/156 |
| 5,993,460 A | 11/1999 | Beitelia et al. |
| 6,036,717 A | 3/2000 | Kelly et al. |
| 6,165,197 A | 12/2000 | Yock |
| 6,234,542 B1 * | 5/2001 | Peterson et al. ............ 285/226 |
| 6,273,899 B1 | 8/2001 | Kramer |
| 6,299,595 B1 | 10/2001 | Dutta et al. |
| 6,309,721 B1 * | 10/2001 | Gladfelter et al. ......... 428/36.1 |

\* cited by examiner

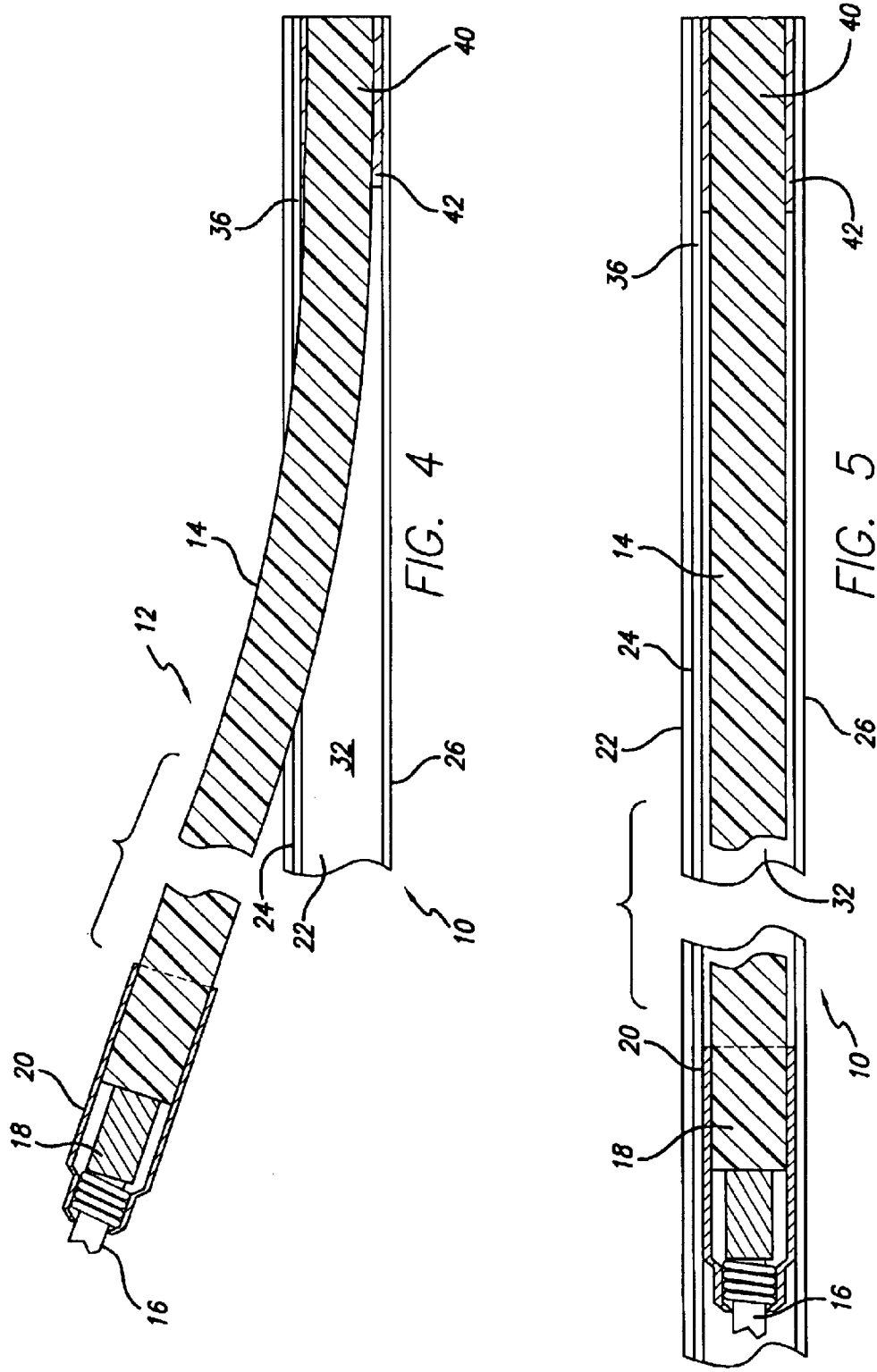

RELOADABLE SHEATH FOR CATHETER SYSTEM FOR DEPLOYING VASOOCCLUSIVE DEVICES

BACKGROUND OF THE INVENTION

This invention relates generally to devices for interventional therapeutic treatment or vascular surgery for treatment of defects in the vasculature, and more particularly concerns a system and method for delivering intravascular interventional devices, such as for treatment of aneurysms.

Vascular interventional devices such as vasoocclusive devices are typically placed within the vasculature of the human body by use of a catheter. Vascular interventional devices such as stents can be placed within an occluded vessel to facilitate blood flow through the vessel, and vasoocclusive devices are typically either placed within a blood vessel to block the flow of blood through a vessel making up that portion of the vasculature through the formation of an embolus, or are placed within an aneurysm stemming from the vessel to form such an embolus within the aneurysm. Stents can have a wide variety of configurations, but generally need to be placed and then released at a desired location within a blood vessel. Vasoocclusive devices used for these procedures can also have a wide variety of configurations, and aneurysms have been treated with external surgically placed clips, detachable vasoocclusive balloons and embolus generating vasoocclusive devices such as one or more vasoocclusive or embolic coils.

The delivery of such vasoocclusive devices has typically been accomplished by a variety of means, including via a catheter in which the device is pushed through an opening at the distal end of the catheter by a pusher to deploy the device. The vasoocclusive devices can be produced in such a way that they will pass through the lumen of a catheter in a linear shape and take on a complex shape as originally formed after being deployed into the area of interest, such as an aneurysm.

Detachable vasoocclusive devices are typically embolic coils fixed to a distal end of a flexible pusher member for delivery of the embolic coils, and may be detached mechanically, electrically or by some other means from the flexible pusher member at the target location. The detachable embolic coils can be delivered to the target location and detached if correctly sized and positioned, or may be withdrawn without being detached if the coils are not correctly sized, are not correctly positioned, or microcatheter positioning is lost. Some available vasoocclusive devices are not reused during a patient procedure if they are removed during the procedure, due to the inability to reload the device into the microcatheter. It would be desirable to provide a system and method for reusing vasoocclusive devices during a clinical procedure after removal from a microcatheter introducer. The present invention meets these and other needs.

SUMMARY OF THE INVENTION

Briefly, and in general terms, the present invention provides for an introducer sheath for vasoocclusive devices that can be loaded onto a vasoocclusive embolic coil assembly after removal of the vasoocclusive embolic coil assembly from a microcatheter, to permit reuse of the vasoocclusive embolic coil assembly during a clinical procedure and to minimize the loss of an otherwise acceptable vasoocclusive embolic coil product.

The present invention accordingly provides for a sheath for a therapeutic vasoocclusive device which includes an assembly of a flexible pusher member and an embolic coil. The sheath includes a hollow, elongated tubular member having opposing upper and lower walls, opposing side walls, and a longitudinal interior channel, and a longitudinal slot formed in the upper wall of the elongated tubular member and extending the length, or majority of the length, of elongated tubular member. The slot has opposing sides with inner side surfaces extending through the upper wall of the elongated tubular member leading to the interior channel permitting introduction of the vasoocclusive device into the interior channel. In one aspect, the upper wall of the elongated tubular member adjacent to the slot has an angled configuration on the outside surface of the hollow, elongated tubular member. The angled configuration on the outside surface of the hollow, elongated tubular member has opposing exterior surfaces forming an interior angle of typically about 110° to 150°.

In another aspect, the lower wall of the hollow, elongated tubular member is about 0.002 to 0.004 inches thick to allow the opposing sides of the slot of the hollow, elongated tubular member to flex outwardly to allow the slot to open to accept the vasoocclusive device. The hollow, elongated tubular member may be formed from a thermoplastic material, such as high density polyethylene, for example.

In one embodiment, the sheath may further include wing members extending outwardly from the angled configuration on the outside surface of the hollow, elongated tubular member to facilitate insertion of the vasoocclusive device into the sheath. The wing members of the angled configuration on the outside surface of the hollow, elongated tubular member have opposing exterior surfaces typically forming an interior angle of about 110° to 150°. In a variation of these embodiments, the sheath may be formed in combination with the vasoocclusive device, the elongated tubular member consisting of a length with no slot attached to a segment of the flexible pusher member to facilitate initiation of loading of the flexible pusher member and embolic coil into the sheath.

These and other aspects and advantages of the invention will become apparent from the following detailed description and the accompanying drawings, which illustrate by way of example the features of the invention.

BRIEF DESCRIPTION OF THE DRAWINGS

FIG. 4 is a longitudinal sectional view of a third embodiment of the reloadable sheath in combination with a vasoocclusive device permanently attached to an end of the reloadable sheath, showing the vasoocclusive device substantially unloaded from the reloadable sheath.

FIG. 5 is a longitudinal sectional view of the reloadable sheath of FIG. 4, showing the vasoocclusive device fully loaded into the reloadable sheath.

DETAILED DESCRIPTION OF THE PREFERRED EMBODIMENTS

Figure 1:
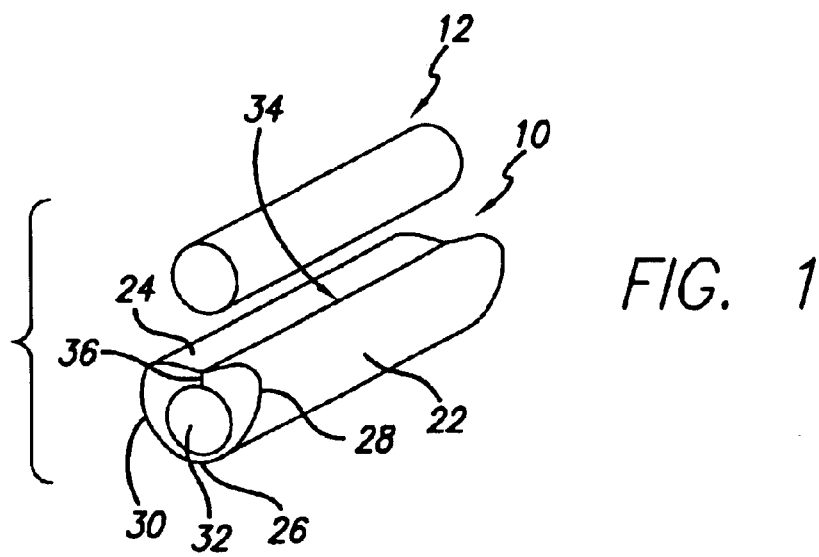
FIG. 1 is a perspective view of a first embodiment of the reloadable sheath for a vasoocclusive device, according to the present invention.

A reloadable sheath 10 for a therapeutic vasoocclusive device 12. The vasoocclusive device typically includes an assembly of a flexible pusher member 14 and an embolic coil 16 (only a portion of which is shown) attached to the flexible pusher member, as illustrated in FIGS. 5 and 6. The flexible pusher member may, for example, include an elongated optical fiber having a distal end 18 sheathed in a tubular collar 20 of shape memory material for retaining the embolic coil on the distal end of the flexible pusher member. The optical fiber can be sized to be quite flexible and bend sufficiently to follow the body lumen. Alternatively, the elongated pusher can be formed of suitable materials for conducting energy, such as radio frequency energy, magnetic energy, electrical energy, or ultrasonic energy, such as an elongated metal member, for example, or of a heat pipe for conducting heat from a heat source. Alternatively, the flexible pusher can consist of a tubular or solid wire construction with attachment to an embolic coil to allow, for example, deployment by mechanical or hydraulic means.

The reloadable sheath is generally formed of a hollow, elongated tubular member 22 having an upper wall 24 and an opposing lower wall 26, opposing side walls 28 and 30, and a longitudinal interior channel 32. The upper wall of the elongated tubular member includes a slot 34 or slit with opposing interior sides 36 having surfaces extending through the upper wall leading to the interior channel, permitting introduction of the vasoocclusive device into the interior channel. The reloadable sheath may have the exemplary dimensions illustrated in FIGS. 3 and set forth in the table below. In the table, "A" indicates a possible longitudinal interior channel dimension (32) and "B" indicates a possible outer diameter sheath dimension.

| System | "A" (in.) | "B" (in.) |
|---|---|---|
| 10 | 0.016 | 0.030 |
| 18 | 0.020 | 0.034 |

Figure 3:
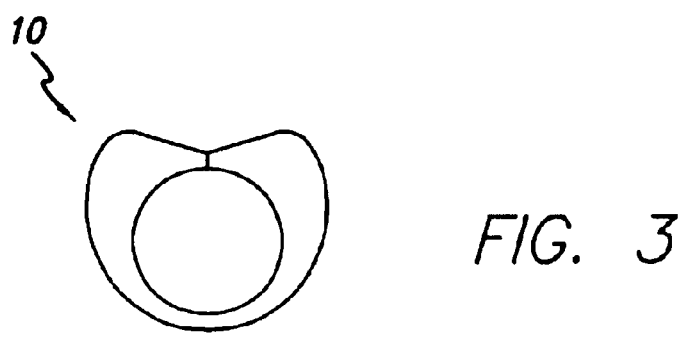
FIG. 3 is a cross-sectional view illustrating dimensions of the reloadable sheath of FIG. 1.

As is best seen in FIGS. 1 and 3 the upper wall of the elongated tubular member adjacent to the slot typically has an outer angled or V-shaped configuration on the outside surface of the tubing, to facilitate loading of the vasoocclusive device into the reloadable sheath. The slot may, for example, have opposing exterior surfaces forming an interior angle of about 110° to 150°. The lower wall of the tubing is typically about 0.002 to 0.004 inches thick to allow opposing sides of the slot of the hollow, elongated tubular member to flex outwardly to allow the slot to open to accept the vasoocclusive device. The configuration allows the flexible pusher member to be inserted into the reloadable sheath by positioning the flexible pusher member and embolic coil assembly over the slot and providing a sliding pressure, such as by a person's thumb, along the length of the flexible pusher member and embolic coil assembly to introduce the flexible pusher member and embolic coil assembly into the sheath. In this embodiment, the sheath is fully removable from the flexible pusher member.

Figure 2:
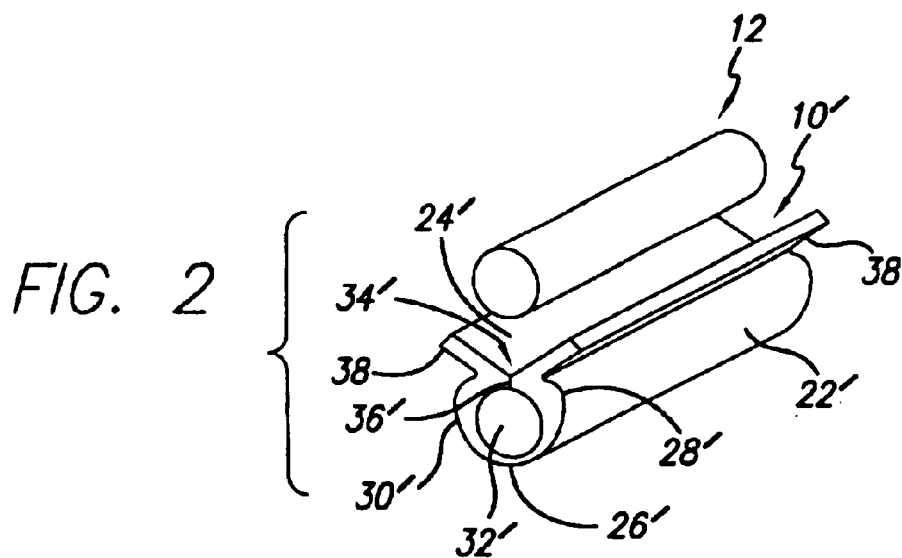
FIG. 2 is a perspective view of a second embodiment of the reloadable sheath for a vasoocclusive device, according to the present invention.

With reference to FIG. 2, in a second embodiment, the present invention provides for a reloadable sheath 10' for a therapeutic vasoocclusive device 12, which typically includes an assembly of a flexible pusher member 14 and an embolic coil 16 described above and illustrated in FIGS. 4 and 5. The reloadable sheath 10' is generally formed of a hollow, elongated tubular member 22' having an upper wall 24' and an opposing lower wall 26', opposing side walls 28' and 30', and a longitudinal interior channel 32'. The upper wall of the elongated tubular member includes a slot 34' with opposing interior sides 36' having surfaces extending through the upper wall leading to the interior channel, permitting introduction of the vasoocclusive device into the interior channel.

The upper wall of the elongated tubular member adjacent to the slot typically has an outer angled or V-shaped configuration on the outside surface of the tubing, to facilitate loading of the vasoocclusive device into the reloadable sheath. The slot may, for example, have opposing exterior surfaces forming an interior angle of about 110° to 150°. The lower wall of the tubing is typically about 0.002 to 0.004 inches thick to allow opposing sides of the slot of the hollow, elongated tubular member to flex outwardly to allow the slot to open to accept the vasoocclusive device. In this embodiment, the upper angled surface portions of the upper wall of the elongated tubular member adjacent to the slot may be formed as outwardly extending walls or wing members 38 to facilitate insertion of the flexible pusher member and embolic coil assembly into the slotted sheath.

With reference to FIGS. 4 and 5, in a variation of the first embodiment, which is equally applicable to the second embodiment, the invention provides for a sheath in combination with a vasoocclusive device which includes an assembly of the flexible pusher member 14 and an embolic coil 16 that is adapted to be inserted into a portion of a vasculature for occluding a portion of the vasculature for use in interventional therapy and vascular surgery. The sheath can remain attached to a segment 40 of the flexible pusher member to facilitate initiation of loading of the flexible pusher member into the sheath. The sheath can be pulled off along the slot until the segment of the sheath without a slot is reached, a segment of length less than the unused working length of the pusher when fully loaded into the microcatheter, for example, about 10 cm. The sheath can then be looped and left attached to the end of the flexible pusher member while the flexible pusher member is loaded into a microcatheter (not shown). If the flexible pusher member is removed without embolic coil detachment, the sheath can be loaded back onto the flexible pusher member starting at the connected location and progressing toward an end of the flexible pusher member. The sheath can then be advanced over the embolic coil to allow the embolic coil to be advanced into the microcatheter at a later time.

In each of the foregoing embodiments, the elongated tubular member forming the reloadable sheath is typically formed from a thermoplastic material. The tubing may be formed from a thermoplastic material such as high density polyethylene, for example. Alternatively, other similar polymeric materials may also be suitable, such as polyurethane, nylons, polyetheretherketone (PEEK), polytetrafluoroethylene (PTFE), polyethylene terephthalate (PET), and the like.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A sheath for a therapeutic vasoocclusive device, the vasoocclusive device including an assembly of a flexible pusher member and an embolic coil, the sheath comprising:

a hollow, elongated tubular member having opposing upper and lower walls, opposing side walls, and a longitudinal interior channel;

a longitudinal slot formed in the upper wall of the elongated tubular member and extending a first portion of the length of elongated tubular member leaving a second portion of the length of the elongated tubular member with no slot, the slot having opposing sides with inner side surfaces extending through the upper wall of the elongated tubular member leading to the interior channel permitting introduction of the vasoocclusive device into the interior channel, wherein the upper wall of the elongated tubular member adjacent to the slot has an angled configuration on the outside surface of the hollow, elongated tubular member.

2. The sheath of claim 1, wherein the angled configuration on the outside surface of the hollow, elongated tubular member has opposing exterior surfaces forming an interior angle of about 110° to 150°.

3. The sheath of claim 1, wherein the lower wall of the hollow, elongated tubular member is about 0.002 to 0.004 inches thick to allow the opposing sides of the slot of the hollow, elongated tubular member to flex outwardly to allow the slot to open to accept the vasoocclusive device.

4. The sheath of claim 1, wherein the hollow, elongated tubular member is formed from a thermoplastic material.

5. The sheath of claim 1, wherein the hollow, elongated tubular member is formed from a high density polyethylene.

6. The sheath of claim 1, further comprising wing members extending outwardly from the angled configuration on the outside surface of the hollow, elongated tubular member to facilitate insertion of the vasoocclusive device into the sheath.

7. The sheath of claim 6, wherein the wing members of the angled configuration on the outside surface of the hollow, elongated tubular member have opposing exterior surfaces forming an interior angle of about 110° to 150°.

* * * * *

UNITED STATES PATENT AND TRADEMARK OFFICE
CERTIFICATE OF CORRECTION

PATENT NO. : 6,716,223 B2
DATED : April 6, 2004
INVENTOR(S) : Eric Leopold and Bruce McEvers It is certified that error appears in the above-identified patent and that said Letters Patent is hereby corrected as shown below:

Title page,
Item [56], References Cited, OTHER PUBLICATIONS, insert
-- Hawkins, et al., *Retrievable Gianturco-Coil Introducer*, Radiology 1986 from the Depts. of Radiology and Neurosurgery, University of Florida Medical Center and Hawk Prototype Equipment, Gainesville, FL. --.

Signed and Sealed this

Fourteenth Day of December, 2004

JON W. DUDAS
*Director of the United States Patent and Trademark Office*